United States Patent
Kasai et al.

(12) 
(10) Patent No.: US 11,946,601 B2
(45) Date of Patent: Apr. 2, 2024

(54) APPARATUS UTILIZING HIGH-PRESSURE AIR

(71) Applicant: DISCO CORPORATION, Tokyo (JP)

(72) Inventors: Tsuyoshi Kasai, Tokyo (JP); Ken Uehara, Tokyo (JP); Satoshi Takahashi, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 265 days.

(21) Appl. No.: 17/445,892

(22) Filed: Aug. 25, 2021

(65) Prior Publication Data

US 2022/0074552 A1     Mar. 10, 2022

(30) Foreign Application Priority Data

Sep. 8, 2020  (JP) .................. 2020-150270

(51) Int. Cl.
*G01N 33/00* (2006.01)
*B01D 46/00* (2022.01)
(Continued)

(52) U.S. Cl.
CPC ........... *F17D 3/16* (2013.01); *B01D 46/0086* (2013.01); *B01D 46/4272* (2013.01);
(Continued)

(58) Field of Classification Search
CPC ......... Y10T 137/7761; Y10T 137/2509; Y10T 137/2499; Y10T 137/271; Y10T 137/8122; Y10T 137/794; Y10T 137/8158; B01D 46/0086; B01D 46/4272; B01D 46/46; G01N 33/0047; G05D 11/138
See application file for complete search history.

(56) References Cited

U.S. PATENT DOCUMENTS 5,569,838 A * 10/1996 Broedel ............... G05D 11/138
                                                        73/23.31
6,155,289 A * 12/2000 Carlsen .............. G05D 16/2013
                                                        137/457
(Continued)

FOREIGN PATENT DOCUMENTS

CN       210386815 U  *  4/2020
CN       210386815 U      4/2020
(Continued)

OTHER PUBLICATIONS

Search report issued in counterpart Singapore patent application No. 10202109484X, dated Oct. 27, 2022.

*Primary Examiner* — Matthew W Jellett

(74) *Attorney, Agent, or Firm* — GREER BURNS & CRAIN, LTD.

(57) ABSTRACT

An apparatus that utilizes high-pressure air therein includes a main body, an air pipe configured to be supplied with high-pressure air from a high-pressure air supply source and supply the high-pressure air into the main body, a filter configured to remove oil contained in the high-pressure air flowing through the air pipe, a gas detector configured to detect an organic gas derived from oil and contained in the high-pressure air that has passed through the filter, and a reporting unit configured to report, when the gas detector detects the organic gas contained in the high-pressure air, that the high-pressure air is mixed with the oil.

11 Claims, 3 Drawing Sheets

(51) Int. Cl.
  *B01D 46/42*    (2006.01)
  *B01D 46/46*    (2006.01)
  *F17D 3/16*    (2006.01)
  *H01L 21/67*    (2006.01)

(52) U.S. Cl.
  CPC ......... *B01D 46/46* (2013.01); *G01N 33/0047* (2013.01); *H01L 21/67092* (2013.01)

(56) References Cited

U.S. PATENT DOCUMENTS

| | | | | |
|---|---|---|---|---|
| 6,387,156 | B1* | 5/2002 | Richardson, Jr. | B23K 26/1435 96/138 |
| 6,439,253 | B1* | 8/2002 | Easton | B67D 7/16 137/88 |
| 6,772,781 | B2* | 8/2004 | Doty | G05D 11/132 137/607 |
| 8,101,420 | B2* | 1/2012 | Conway | G01N 33/1846 137/561 R |
| 10,828,986 | B2* | 11/2020 | Faraji | B01D 46/0086 |
| 10,958,991 | B2* | 3/2021 | Scope | F01P 11/06 |
| 11,435,764 | B1* | 9/2022 | Smirnov | G01F 1/698 |
| 2013/0148461 | A1* | 6/2013 | Li | G01N 30/34 366/152.2 |

FOREIGN PATENT DOCUMENTS

| | | | |
|---|---|---|---|
| JP | 2009246098 A | 10/2009 | |
| JP | 2010036275 A | 2/2010 | |
| JP | 2012002604 A | 1/2012 | |

\* cited by examiner

APPARATUS UTILIZING HIGH-PRESSURE AIR

BACKGROUND OF THE INVENTION

Field of the Invention

The present invention relates to an apparatus that utilizes high-pressure air therein, with an air pipe connected thereto as a line for supplying high-pressure air.

Description of the Related Art

Device chips for use in electronic equipment including mobile phones, computers, etc., are manufactured from wafers made of a material such as silicon (Si) or silicon carbide (SiC). Specifically, a plurality of intersection projected dicing lines are established on the face side of a wafer, and devices such as integrated circuits (ICs) or large-scale-integration (LSI) circuits are formed in respective areas demarcated on the face side by the projected dicing lines. Then, the wafer is thinned down by being ground from its reverse side, and divided along the projected dicing lines into individual device chips. In a step of producing individual device chips from wafers, there are used a grinding apparatus for grinding the wafers, a cutting apparatus for dividing the wafers, a laser processing apparatus, and so on (see, for example, JP 2009-246098A, JP 2010-036275A, and JP 2012-002604A). These apparatuses utilize high-pressure air for actuating suction sources that apply suction forces to chuck tables for holding wafers under suction, cleaning wafers that have been processed, actuating bearings for rotating spindles, and in various other applications.

SUMMARY OF THE INVENTION

An air compressor for use as a high-pressure air supply source is disposed outside of an apparatus involved in the step of producing individual device chips from wafers. The air compressor compresses air and supplies compressed high-pressure air through an air pipe to the apparatus. At this time, the high-pressure air may possibly be mixed with oil such as lubricating oil used in the air compressor. If the high-pressure air supplied to the apparatus is mixed with oil, then the oil tends to be applied to a wafer processed by the apparatus to lower the quality of the wafer, applied to an optical system in the apparatus to degrade the optical system, or applied to an actuating mechanism to cause an operation failure. One solution is to remove the oil from the high-pressure air with a filter placed in the air pipe through which the high-pressure air flows. However, the filter may be contaminated by the oil so much that the filter may no longer be able to remove the oil from the high-pressure air and that the oil trapped by the filter may be released from the filter. If the apparatus continues to operate regardless of such a filter malfunction, oil-induced problems inflicted on the apparatus may grow larger while the apparatus supervisor remains unnoticed, possibly resulting in a large loss.

It is therefore an object of the present invention to provide an apparatus that is capable of monitoring high-pressure air supplied thereto and reporting when the high-pressure air is mixed with oil.

In accordance with an aspect of the present invention, there is provided an apparatus that utilizes high-pressure air therein. The apparatus includes a main body, an air pipe configured to be supplied with high-pressure air from a high-pressure air supply source and supply the high-pressure air into the main body, a filter configured to remove oil contained in the high-pressure air flowing through the air pipe, a gas detector configured to detect an organic gas derived from oil and contained in the high-pressure air that has passed through the filter, and a reporting unit configured to report, when the gas detector detects the organic gas contained in the high-pressure air, that the high-pressure air is mixed with the oil.

Preferably, the high-pressure air supply source that supplies the air pipe with the high-pressure air is an air compressor.

Preferably, the apparatus further includes a shut-off valve configured to stop the flow of the high-pressure air in the air pipe if the reporting unit reports that the high-pressure air is mixed with the oil.

Preferably, the apparatus further includes an auxiliary gas detector disposed in the air pipe and configured to detect an organic gas contained in the high-pressure air prior to passing through the filter.

The apparatus according to the aspect of the present invention includes the filter configured to remove oil contained in the high-pressure air flowing through the air pipe and the gas detector configured to detect an organic gas derived from oil and contained in the high-pressure air that has passed through the filter. The apparatus further includes the reporting unit configured to report, when the gas detector detects the organic gas contained in the high-pressure air, that the high-pressure air is mixed with the oil.

If the high-pressure air that has passed through the filter contains the organic gas, it is understood that the filter has been contaminated to the extent that the high-pressure air is mixed with oil. Since the high-pressure air mixed with oil would otherwise be introduced into the apparatus, the air pipe may be shut off, for example, to prevent the oil from entering the apparatus, and the contaminated filter may be replaced with a fresh filter that is effective to sufficiently remove the oil from the high-pressure air. Inasmuch as the operator of the apparatus according to the present invention can thus deal with oil-induced problems before they become worse in response to a report from the reporting unit, the expenditure of time and cost required to recover the filter or other components may be reduced.

Consequently, according to the present invention, there is provided an apparatus capable of monitoring supplied high-pressure air and reporting when the high-pressure air is mixed with oil.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

Figure 1:
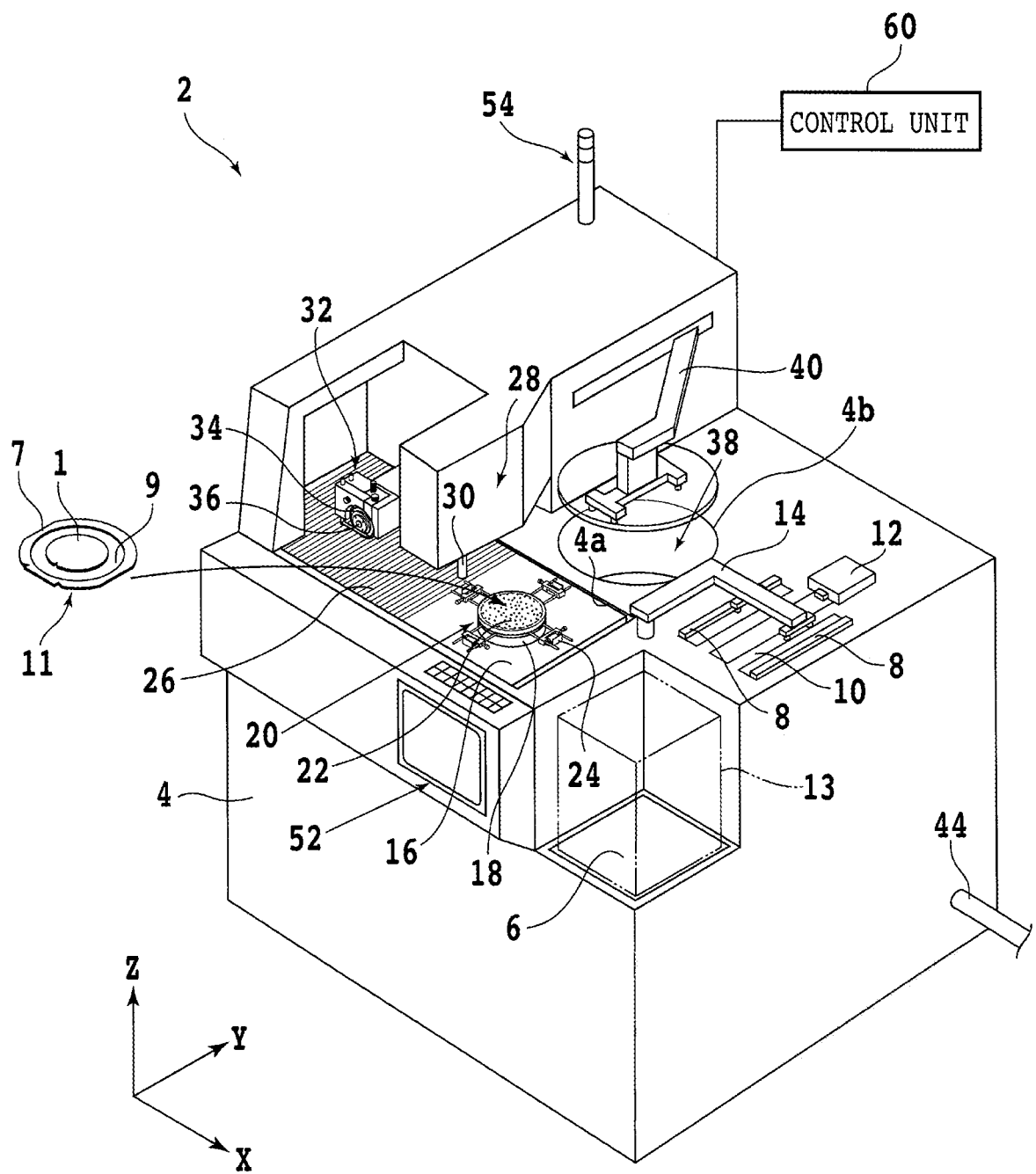
FIG. 1 is a perspective view schematically illustrating an apparatus that is supplied with high-pressure air and a high-pressure air supply source.

A preferred embodiment of the present invention will hereinafter be described with reference to the accompanying drawings. Identical parts are denoted by identical reference signs throughout views. FIG. 1 schematically illustrates, in perspective, an apparatus 2 according to the present embodiment and a frame unit 11 including a wafer 1 to be processed by the apparatus 2. The frame unit 11 includes an annular frame 7 with an opening defined centrally therein, a dicing tape 9 affixed to the frame 7 to close the opening, and the wafer 1 disposed on the dicing tape 9 within the opening. The wafer 1 is, for example, a substrate shaped as a substantially circular plate made of a material such as Si, SiC, gallium nitride (GaN), gallium arsenide (GaAs), or other semiconductor materials, or a material such as sapphire, glass, or quartz. The wafer 1 has a face side including a plurality of areas demarcated by a plurality of intersecting projected dicing lines. Devices such as ICs, LSI circuits, or light emitting diodes (LEDs) are disposed respectively in the areas demarcated by the projected dicing lines. The wafer 1 is divided along the projected dicing lines into individual device chips including the respective devices.

The apparatus 2 is, for example, a cutting apparatus having an annular cutting blade. The wafer 1 is divided by the cutting apparatus, for example. However, the apparatus 2 is not limited to a cutting apparatus and may be a laser processing apparatus for applying a laser beam to a workpiece such as the wafer 1 to process the workpiece or a grinding apparatus for grinding a workpiece such as the wafer 1 with grindstones. According to the present embodiment, the apparatus 2 as a cutting apparatus will be described in detail below.

Before being loaded into the apparatus 2, the wafer 1 may integrally be combined with the dicing tape 9 and the frame 7, providing the frame unit 11 including the wafer 1, the dicing tape 9, and the frame 7. When the wafer 1 of the frame unit 11 is divided into individual device chips by the apparatus 2, the individual device chips are supported on the dicing tape 9. Thereafter, the dicing tape 9 is expanded to increase a distance between adjacent ones of the device chips, making it easy to pick up the device chips from the dicing tape 9.

As illustrated in FIG. 1, a cassette table 6 on which a cassette 13 is placed is disposed in a corner of a main body 4 of the apparatus 2. The cassette 13 houses a plurality of frame units 11 therein and allows frame units 11 to be unloaded therefrom and loaded therein one at a time. The cassette table 6 is vertically movable upwardly and downwardly (in Z-axis directions) by a lifting and lowering mechanism (not illustrated). In FIG. 1, the cassette 13 placed on the cassette table 6 has its profile indicated by two-dot-and-dash lines. A temporary rest table 10 is disposed in a position on an upper surface of the main body 4 adjacent to the cassette table 6. The temporary rest table 10 includes a pair of guide rails 8 movable toward and away from each other in X-axis directions while being kept parallel to each other along Y-axis directions (leftward and rightward directions or indexing feed directions). An unloading unit 12 for unloading a frame unit 11 out of the cassette 13 placed on the cassette table 6 is disposed in a position on the upper surface of the main body 4 adjacent to the temporary rest table 10. The unloading unit 12 has a gripper on its front face for gripping the frame 7 of the frame unit 11.

For unloading a frame unit 11 from the cassette 13, the unloading unit 12 is moved toward the cassette 13, causes the gripper to grip the frame 7 of the frame unit 11 in the cassette 13, and is then moved away from the cassette 13. The frame unit 11 gripped by the gripper is now placed onto the temporary rest table 10. At this time, the guide rails 8 are moved toward each other in the X-axis directions to sandwich the frame 7, whereupon the frame unit 11 is positioned in a predetermined position on the temporary rest table 10.

The main body 4 has an opening 4a defined in the upper surface thereof at a position adjacent to the cassette table 6. The opening 4a is oblong in the X-axis directions (forward and rearward directions or processing feed directions). The opening 4a accommodates therein a ball-screw-type X-axis moving mechanism (processing feed unit), which is not illustrated, and a bellows-like dust-resistant and drip-resistant cover 26 covering an upper portion of the X-axis moving mechanism. The X-axis moving mechanism is connected to a lower portion of an X-axis movable table 16 and has a function of moving the X-axis movable table 16 in the X-axis directions. The X-axis movable table 16 is movable between a loading/unloading area near the cassette table 6 and a processing area below a cutting unit 32, to be described later, for example.

The X-axis movable table 16 supports thereon a table base 18 and a chuck table 20 disposed on the table base 18. The chuck table 20 has an upper surface acting as a holding surface 22 for holding a frame unit 11 including a wafer 1 thereon. A plurality of clamps 24 for clamping the frame 7 of a frame unit 11 are disposed radially outwardly of the chuck table 20 and angularly spaced at intervals around the chuck table 20. The chuck table 20 is movable in the X-axis directions by the X-axis moving mechanism. The chuck table 20 includes a porous member exposed on the holding surface 22. A suction channel (not illustrated) is defined in the chuck table 20 and has an end connected to the porous member and the other end connected to a suction source (not illustrated). The suction source is, for example, an aspirator that generates suction forces when supplied with high-pressure air.

A frame unit 11 placed on the temporary rest table 10 is delivered therefrom to the chuck table 20 by a first delivery unit 14 disposed in a position on the upper surface of the main body 4 adjacent to the temporary rest table 10 and the opening 4a. The first delivery unit 14 has a shaft that protrudes upwardly from the upper surface of the main body 4 and is vertically movable and rotatable about its central axis, an arm extending horizontally from the upper end of the shaft, and a holder disposed on the lower surface of a distal end portion of the arm. The holder holds the frame unit 11 under suction forces generated by using high-pressure air supplied to the first delivery unit 14, for example.

For delivering a frame unit 11 from the temporary rest table 10 to the chuck table 20 by using the first delivery unit 14, the X-axis movable table 16 is moved to position the chuck table 20 in the loading/unloading area. Then, the holder of the first delivery unit 14 holds the frame 7 of the frame unit 11 placed on the temporary rest table 10, and then, the shaft of the first delivery unit 14 is moved upwardly to lift the frame unit 11 and rotated to move the frame unit 11 to a position above the chuck table 20. Thereafter, the shaft is moved downwardly to lower the frame unit 11 onto the holding surface 22 of the chuck table 20. The clamps 24 clamp the frame 7 of the frame unit 11 in position, and the chuck table 20 holds the wafer 1 on the holding surface 22 with the dicing tape 9 interposed therebetween, under suction forces applied to the porous member from the suction source.

The apparatus 2 also includes a support structure 28 mounted on the upper surface of the main body 4 in overhanging relation to the opening 4a above the path along which the X-axis movable table 16 is movable from the loading/unloading area to the processing area. The support structure 28 supports thereon an image capturing unit 30 facing downwardly. The image capturing unit 30 captures an image of the face side of a wafer 1 held on the chuck table 20 that has moved to the processing area below the cutting unit 32, and detects the position and orientation of projected dicing lines 3 on the face side of the wafer 1.

The cutting unit (processing unit) 32 disposed above the processing area cuts (processes) the wafer 1 of the frame unit 11 held on the chuck table 20. The cutting unit 32 includes a cutting blade 34 having an annular grindstone on its outer circumferential edge portion and a spindle 36 with the cutting blade 34 mounted on a distal end portion thereof, the spindle 36 being rotatable about its central axis extending along the Y-axis directions. The spindle 36 is rotatably supported by bearings that utilize high-pressure air. The spindle 36 has a proximal end portion coupled to a rotary actuator (not illustrated) such as an electric motor. The wafer 1 of the frame unit 11 held on the chuck table 20 is cut into individual device chips by the cutting blade 34 as it rotates and cuts into the wafer 1 along all the projected dicing lines. After the wafer 1 has been cut by the cutting unit 32, the chuck table 20 is moved to the loading/unloading area by the X-axis moving mechanism.

The main body 4 also has an opening 4b defined in the upper surface thereof at a position adjacent to the temporary rest table 10 and the opening 4a. The opening 4b accommodates therein a cleaning unit 38 for cleaning a frame unit 11 that has been processed. The cleaning unit 38 includes a spinner table for holding the frame unit 11 thereon. The spinner table has a lower portion coupled to a rotary actuator (not illustrated) that rotates the spinner table about its central axis at a predetermined speed.

The apparatus 2 includes a second delivery unit 40 for delivering a frame unit 11 from the chuck table 20 positioned in the loading/unloading area to the cleaning unit 38. The second delivery unit 40 has an arm movable along the Y-axis directions and a holder disposed on the lower surface of a distal end portion of the arm. For delivering a frame unit 11 from the chuck table 20 to the cleaning unit 38 by using the second delivery unit 40, the holder of the second delivery unit 40 holds the frame unit 11. Then, the arm is moved along one of the Y-axis directions, and the holder places the frame unit 11 onto the spinner table of the cleaning unit 38. Thereafter, the spinner table holds the frame unit 11 thereon, and the cleaning unit 38 cleans the wafer 1.

For cleaning a wafer 1 with the cleaning unit 38, while the spinner table is being rotated, a cleaning fluid (typically a mixture of water and high-pressure air) is ejected toward the face side of the wafer 1. Then, high-pressure air is supplied to the face side of the wafer 1, drying the wafer 1. After the wafer 1 has been cleaned and dried, the frame unit 11 is placed back into the cassette 13 placed on the cassette table 6. For placing the frame unit 11 into the cassette 13, the first delivery unit 14 is used to deliver the frame unit 11 from the cleaning unit 38 to the temporary rest table 10. The gripper of the unloading unit 12 grips the frame 7 of the frame unit 11 on the temporary rest table 10, and the unloading unit 12 is moved toward the cassette 13 and pushes the frame unit 11 into the cassette 13.

The apparatus 2 operates as follows. A frame unit 11 to be processed is unloaded from the cassette 13 and held under suction on the chuck table 20. The wafer 1 of the frame unit 11 on the chuck table 20 is processed by the cutting unit 32. Thereafter, the frame unit 11 is cleaned by the cleaning unit 38 and housed in the cassette 13 again. Actually, the apparatus 2 operates to process a plurality of wafers 1 in succession by unloading the frame units 11 from the cassette 13 one after another and cutting the wafers 1 successively on the chuck table 20 by the cutting unit 32.

The apparatus 2 includes a control unit 60 for controlling the components of the apparatus 2. The control unit includes a computer including a processor such as a central processing unit (CPU) and a storage device such as a flash memory. The control unit 60 functions as specific means realized by a cooperation of software such as programs stored in the storage device and the processor (hardware source) when the processor executes the software.

Figure 2A:
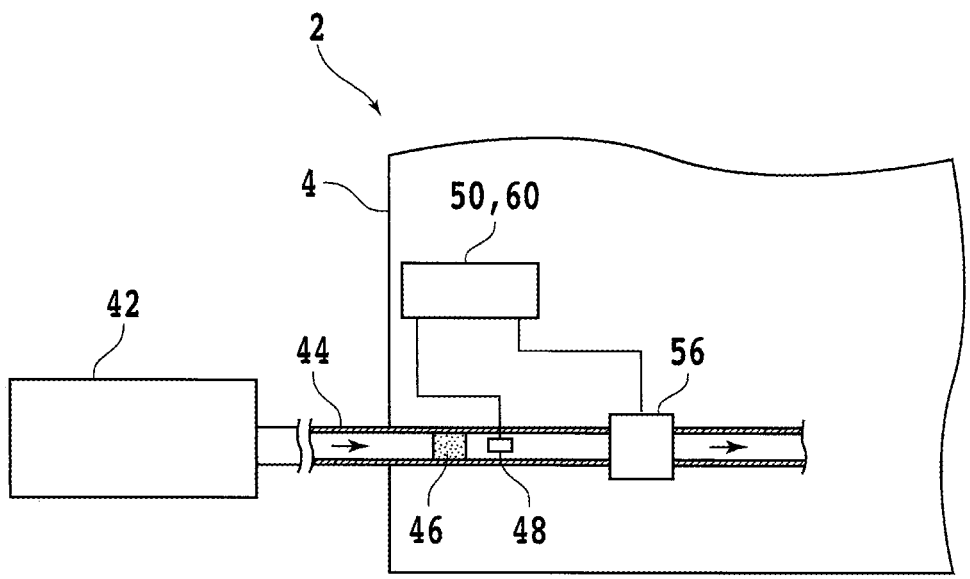
FIG. 2A is a view schematically illustrating an example of air piping incorporated in the apparatus.

As described above, the apparatus 2 utilizes high-pressure air in various applications at various locations thereon. FIG. 2A schematically illustrates a high-pressure air supply source 42, the apparatus 2, and an air pipe 44 interconnecting the high-pressure air supply source 42 and the apparatus 2. High-pressure air is generated when an air compressor functioning as the high-pressure air supply source 42 compresses air, for example. The generated high-pressure air is supplied to the apparatus 2 through the air pipe 44 such as a high-pressure tube made of urethane, vinyl chloride, or the like.

The high-pressure air may possibly be mixed with oil such as lubricating oil used in the air compressor. If the high-pressure air supplied to the apparatus 2 is mixed with oil, then the oil tends to be applied to a wafer 1 processed by the apparatus 2, possibly causing an electrical characteristic failure to device chips produced from the wafer 1. In addition, oil may possibly be applied to the image capturing unit 30, and the image capturing unit 30 may not detect projected dicing lines of the wafer 1 appropriately. Further, oil may possibly be applied to an actuating mechanism, resulting in an operation failure. According to a solution, a filter 46 is placed in the air pipe 44 through which the high-pressure air flows, for removing oil contained in the high-pressure air that has passed through the high-pressure air supply source 42 with use of the filter 46.

However, while the apparatus 2 is operating for a long period of time, the filter 46 may be contaminated by the oil so much that the oil trapped by the filter 46 may be released from the filter 46 and that the filter 46 may fail to sufficiently remove the oil contained in the high-pressure air supplied from the high-pressure air supply source 42 to the air pipe 44. According to the apparatus 2 of the present embodiment, the high-pressure air supplied from the high-pressure air supply source 42 to the air pipe 44 is monitored to detect the inclusion of oil mixed with the high-pressure air. If the contamination of the filter 46 goes on and the high-pressure air that has passed through the filter 46 remains mixed with oil, an organic gas derived from the oil is also contained in the high-pressure air. The apparatus 2 according to the present embodiment monitors the high-pressure air that has passed through the filter 46 and detects and reports that the high-pressure air is mixed with oil, by detecting an organic gas contained in the high-pressure air.

As illustrated in FIG. 2A, the apparatus 2 according to the present embodiment includes a gas detector 48 for detecting an organic gas contained in the high-pressure air that has passed through the filter 46. The gas detector 48 is installed on an inner wall surface of the air pipe 44. The gas detector 48 has a function to monitor the high-pressure gas flowing through the air pipe 44 and output information regarding various components contained in the high-pressure gas to a reporting unit 50 to be described below. The gas detector 48 may be a gas sensor "SGP30" manufactured by Sensirion Co., Ltd., for example.

The apparatus 2 according to the present embodiment further includes the reporting unit 50 for reporting that the high-pressure air is mixed with oil, at the time when the gas detector 48 detects an organic gas contained in the high-pressure air. The reporting unit 50 is realized by a function of the control unit 60 of the apparatus 2, for example. The reporting unit 50 may report that the high-pressure air is mixed with an organic gas, instead of reporting that the high-pressure air is mixed with oil. As illustrated in FIG. 1, the apparatus 2 may include a display monitor 52 for displaying various pieces of information. The apparatus 2 may further include a warning lamp 54 energizable to turn on lamp segments in predetermined colors depending on different states of the apparatus 2, and/or a speaker (not illustrated) for issuing a warning sound. If the gas detector 48 detects that the high-pressure air supplied from the high-pressure air supply source 42 to the apparatus 2 contains an organic gas, then the reporting unit 50 displays warning information on the display monitor 52, for example. The reporting unit 50 may also energize the warning lamp 54 to turn on a lamp segment in red indicating a malfunctioning state. The reporting unit 50 may further energize the speaker to give off a warning sound. In this manner, the reporting unit 50 reports to the operator of the apparatus 2 that the high-pressure air contains an organic gas and the high-pressure air is thus mixed with oil.

The apparatus 2 may also include a shut-off valve 56 for stopping the flow of high-pressure air in the air pipe 44. The shut-off valve 56 is, for example, a solenoid-operated valve electrically connected to the reporting unit 50 and can be opened and closed by commands from the reporting unit 50. If the gas detector 48 detects that the high-pressure air supplied from the high-pressure air supply source 42 to the apparatus 2 contains an organic gas, then the reporting unit 50 actuates the shut-off valve 56 to stop the flow of high-pressure air in the air pipe 44, thereby preventing oil from entering the apparatus 2.

If an organic gas contained in the high-pressure air is detected, then the reporting unit 50 that is implemented by the control unit 60 shuts down the apparatus 2 as soon as possible in order to avoid spreading problems to various parts of the apparatus 2. The operator checks the high-pressure air supply source 42 or replaces the filter 46, and activates the apparatus 2 again. In a case where the apparatus 2 stops operating while the high-pressure air is not being supplied, wafers 1 or workpieces are not processed by the apparatus 2, resulting in a reduction in the efficiency with which the workpieces are processed. To alleviate the efficiency decrease, the apparatus 2 may be supplied with high-pressure air from another high-pressure air supply source and may be kept in continuous operation.

Figure 2B:
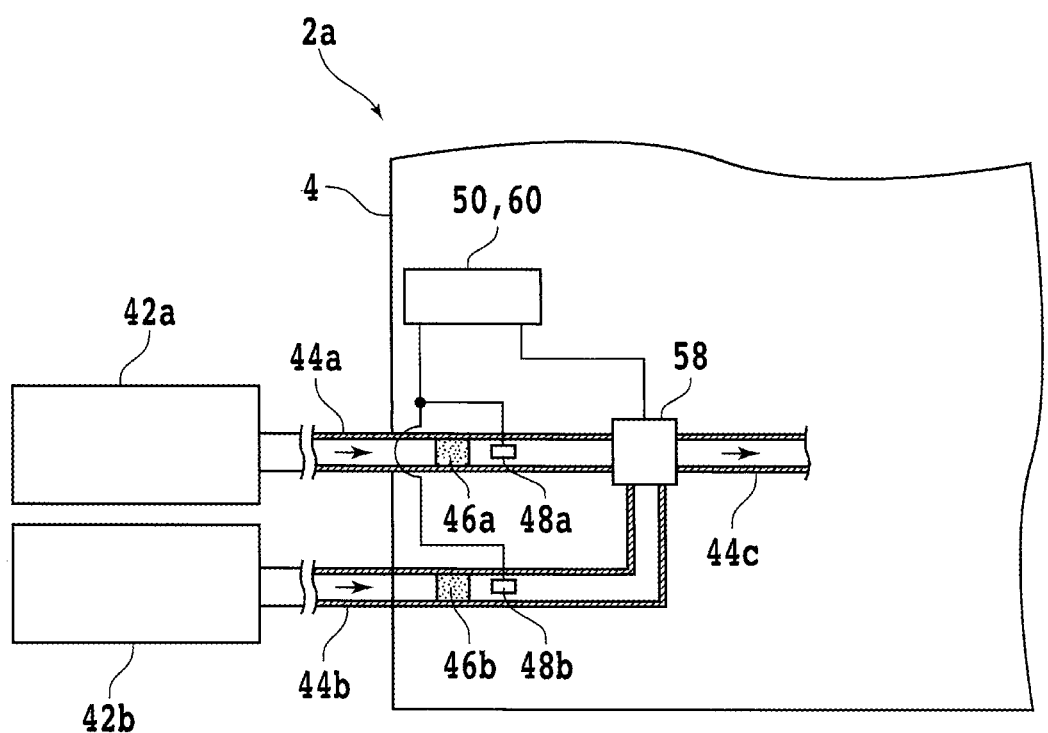
FIG. 2B is a view schematically illustrating an example of air piping incorporated in a modified apparatus.

FIG. 2B schematically illustrates an apparatus 2a according to a modification of the above embodiment that is supplied with high-pressure air from two supply systems. The apparatus 2a illustrated in FIG. 2B includes a first air pipe 44a through which high-pressure air is supplied from a first high-pressure air supply source 42a to the apparatus 2a and a second air pipe 44b through which high-pressure air is supplied from a second high-pressure air supply source 42b to the apparatus 2a.

The first air pipe 44a has a first filter 46a for removing oil contained in high-pressure air supplied from the first high-pressure air supply source 42a and a first gas detector 48a for detecting an organic gas contained in the high-pressure air that has passed through the first filter 46a. The first gas detector 48a is electrically connected to the reporting unit 50. The second air pipe 44b has a second filter 46b for removing oil contained in high-pressure air supplied from the second high-pressure air supply source 42b and a second gas detector 48b for detecting an organic gas contained in the high-pressure air that has passed through the second filter 46b. The second gas detector 48b is electrically connected to the reporting unit 50.

A three-way valve 58 is connected to a portion of the first air pipe 44a downstream of the first gas detector 48a and a portion of the second air pipe 44b downstream of the second gas detector 48b. The three-way valve 58 is connected to an inner pipe 44c extending into the main body 4 of the apparatus 2a, for selectively connecting the first air pipe 44a and the second air pipe 44b to the inner pipe 44c.

For example, when the three-way valve 58 connects the first air pipe 44a to the inner pipe 44c, high-pressure air from the first high-pressure air supply source 42a is supplied to the apparatus 2a. At this time, the first gas detector 48a monitors the high-pressure air flowing through the first air pipe 44a. If an organic gas contained in the high-pressure air is detected by the first gas detector 48a, the reporting unit 50 reports to the operator that the high-pressure air is mixed with oil, and switches the three-way valve 58 to supply high-pressure air from the second high-pressure air supply source 42b to the apparatus 2a. In this case, the high-pressure air keeps being supplied to the apparatus 2a even during a step of replacing the first filter 46a and a step of inspecting the first high-pressure air supply source 42a. Consequently, it is not necessary to stop processing wafers 1 or workpieces on the apparatus 2a while the first high-pressure air supply source 42a, the first filter 46a, etc., are being recovered.

Thereafter, the second gas detector 48b monitors the high-pressure air flowing through the second air pipe 44b. If an organic gas contained in the high-pressure air is detected by the second gas detector 48b, the reporting unit 50 switches the three-way valve 58 again to supply high-pressure air from the first high-pressure air supply source 42a to the apparatus 2a. As described above, even in a case where one of the two high-pressure air supply systems runs into trouble, the other high-pressure air supply system is able to keep supplying high-pressure air to the apparatus 2a while efforts are being made to recover the defective high-pressure air supply system. The apparatus 2a may be combined with three or more high-pressure air supply systems that can selectively be enabled to supply high-pressure air to the apparatus 2a.

As described above, the apparatus according to the above embodiment and modification can monitor supplied high-pressure air and detect an organic gas contained in the high-pressure air. Therefore, even if the high-pressure air is mixed with oil such as lubricating oil used in the high-pressure air supply sources 42, 42a, and 42b, the operator or the like can deal with oil-induced problems before they spread into the apparatus and become worse.

Figure 3:
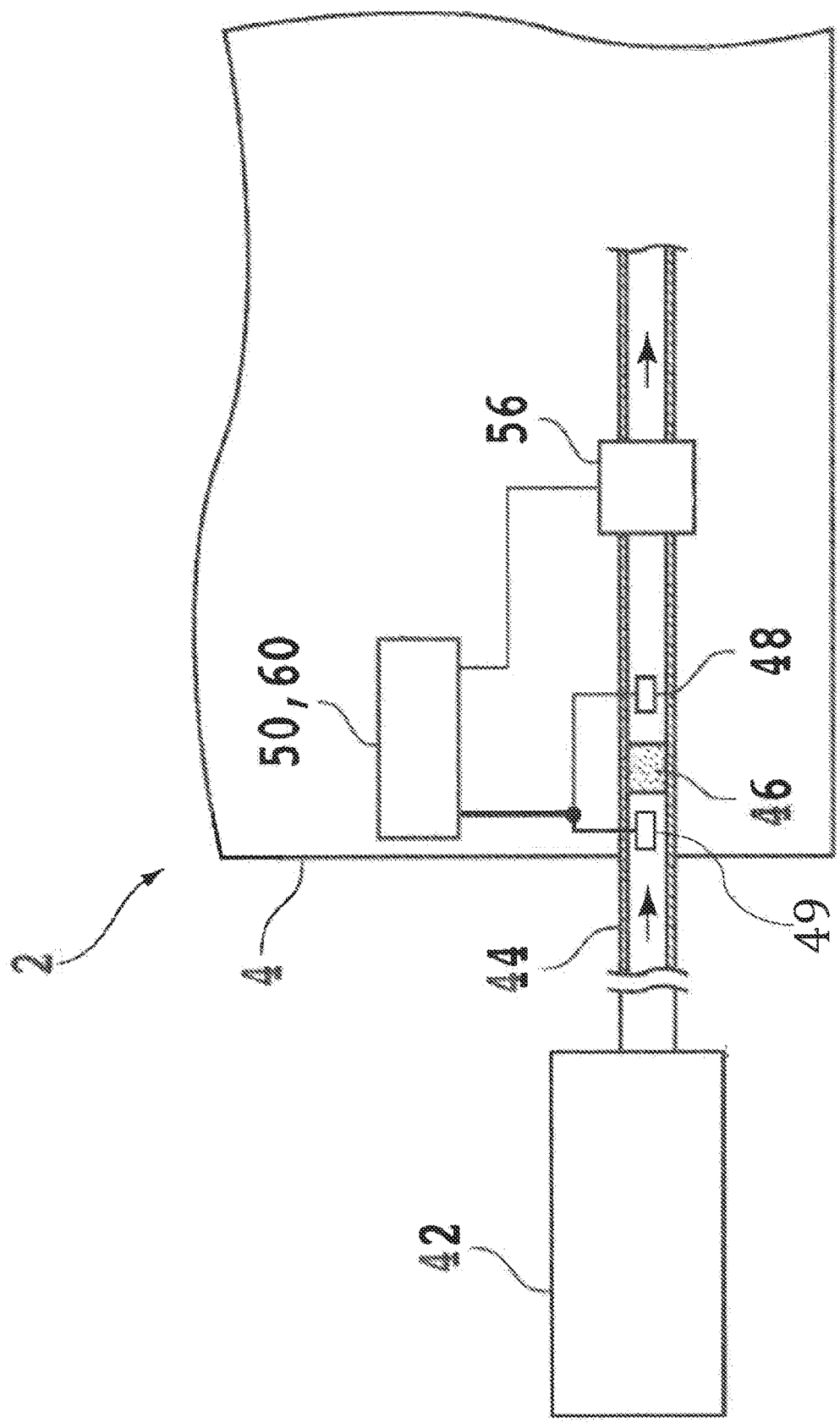
FIG. 3 is a view schematically illustrating an example of air piping incorporated in another modified apparatus.

According to the above embodiment, the gas detector 48 is disposed in the air pipe 44 downstream of the filter 46 that removes oil contained in the high-pressure air. However, the apparatus according to the present invention is not limited to such details. In other words, the apparatus 2 may include, as shown in FIG. 3, in addition to the gas detector 48, an auxiliary gas detector 49 disposed upstream of the filter 46 in the air pipe 44. As the gas detector 48 and the auxiliary gas detector 49 monitor the high-pressure air downstream and upstream, respectively, of the filter 46, it is easier to identify where oil occurs. For example, if the gas detector 48 detects an organic gas contained in the high-pressure air and the auxiliary gas detector 49 detects no organic gas, then the operator can confirm that the filter 46 is so contaminated that the high-pressure air that has passed through the filter 46 is mixed with oil. If the auxiliary gas detector 49 detects an organic gas, then the operator knows that the high-pressure air supply source 42 is malfunctioning in some way.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. An apparatus that utilizes high-pressure air therein, comprising:
   a main body;
   an air pipe configured to be supplied with high-pressure air from a high-pressure air supply source and supply the high-pressure air into the main body;
   a filter configured to remove oil contained in the high-pressure air flowing through the air pipe;
   a gas detector configured to detect an organic gas derived from oil and contained in the high-pressure air that has passed through the filter; and
   a reporting unit configured to report to an operator of the apparatus, when the gas detector detects the organic gas contained in the high-pressure air, that the high-pressure air is mixed with the oil.

2. The apparatus according to claim 1, wherein the high-pressure air supply source that supplies the air pipe with the high-pressure air is an air compressor.

3. The apparatus according to claim 1, further comprising:
   a shut-off valve configured to stop the flow of the high-pressure air in the air pipe if the reporting unit reports that the high-pressure air is mixed with the oil.

4. An apparatus that utilizes high-pressure air therein, comprising:
   a main body;
   an air pipe configured to be supplied with high-pressure air from a high-pressure air supply source and supply the high-pressure air into the main body;
   a filter configured to remove oil contained in the high-pressure air flowing through the air pipe;
   a gas detector configured to detect an organic gas derived from oil and contained in the high-pressure air that has passed through the filter;
   a reporting unit configured to report to an operator of the apparatus, when the gas detector detects the organic gas contained in the high-pressure air, that the high-pressure air is mixed with the oil; and
   an auxiliary gas detector disposed in the air pipe and configured to detect an organic gas contained in the high-pressure air prior to passing through the filter.

5. The apparatus according to claim 1, wherein the main body includes a cassette table configured and arranged to receive a cassette including a plurality of wafers therein.

6. The apparatus according to claim 1, further comprising:
   a second air pipe configured to be supplied with high-pressure air from a second high-pressure air supply source and to supply the high-pressure air into the main body;
   a second filter configured to remove oil contained in the high-pressure air flowing through the second air pipe;
   a second gas detector configured to detect an organic gas derived from oil and contained in the high-pressure air that has passed through the second filter; and
   a three-way valve connected to both:
   the air pipe at a location downstream of the filter; and
   the second air pipe at a location downstream of the second air filter,
   wherein the three-way valve is configured and arranged to switch the high pressure air flow between the air pipe and the second air pipe based on whether the gas detector or the second gas detector has detected the organic gas within the high pressure air.

7. The apparatus according to claim 1, wherein the reporting unit reports to the operator by displaying warning information on a display monitor.

8. The apparatus according to claim 1, wherein the reporting unit reports to the operator by turning on a warning light.

9. The apparatus according to claim 4, wherein the reporting unit reports to the operator by displaying warning information on a display monitor.

10. The apparatus according to claim 4, wherein the reporting unit reports to the operator by turning on a warning light.

11. The apparatus according to claim 1, wherein the gas detector comprises a gas sensor.

* * * * *